United States Patent
Hoenick et al.

(10) Patent No.: US 10,628,554 B2
(45) Date of Patent: Apr. 21, 2020

(54) PRESCRIPTION FILLING BY IMAGE

(71) Applicant: CVS Pharmacy, Inc., Woonsocket, RI (US)

(72) Inventors: John Robert Hoenick, Providence, RI (US); William A. McKibbin, Barrington, RI (US); Jeffrey M. Hoffman, Medfield, MA (US); Dustin W. Humphreys, East Greenwich, RI (US)

(73) Assignee: CVS Pharmacy, Inc., Woonsocket, RI (US)

( * ) Notice: Subject to any disclaimer, the term of this patent is extended or adjusted under 35 U.S.C. 154(b) by 757 days.

(21) Appl. No.: 14/829,172

(22) Filed: Aug. 18, 2015

(65) Prior Publication Data

US 2017/0053094 A1  Feb. 23, 2017

(51) Int. Cl.
| | | |
|---|---|---|
| *G06F 19/00* | (2018.01) | |
| *G16H 20/10* | (2018.01) | |
| *G06Q 50/22* | (2018.01) | |
| *G06Q 10/10* | (2012.01) | |
| *G06Q 10/08* | (2012.01) | |
| *G06K 9/00* | (2006.01) | |

(52) U.S. Cl.
CPC ......... *G06F 19/3456* (2013.01); *G06K 9/00* (2013.01); *G06Q 10/083* (2013.01); *G06Q 10/10* (2013.01); *G06Q 50/22* (2013.01); *G16H 20/10* (2018.01)

(58) Field of Classification Search
None
See application file for complete search history.

(56) References Cited

U.S. PATENT DOCUMENTS

| | | |
|---|---|---|
| 6,493,427 B1 | 12/2002 | Kobylevsky et al. |
| 7,058,584 B2 | 6/2006 | Kosinsi et al. |
| 7,337,971 B2 | 3/2008 | Melick et al. |
| 8,626,530 B1 | 1/2014 | Tran et al. |
| 8,694,332 B2 | 4/2014 | Martin et al. |
| 8,891,812 B2 | 11/2014 | Obrea et al. |
| 2003/0225595 A1* | 12/2003 | Helmus ............... G06Q 10/063 705/2 |
| 2004/0019794 A1 | 1/2004 | Moradi et al. |
| 2008/0015897 A1 | 1/2008 | Moradi et al. |
| 2008/0177787 A1 | 7/2008 | Karamchedu et al. |
| 2009/0006126 A1 | 1/2009 | Champigny |
| 2012/0065997 A1 | 3/2012 | Farooq et al. |
| 2012/0253832 A1* | 10/2012 | John ..................... G06Q 10/00 705/2 |
| 2014/0281871 A1* | 9/2014 | Brunner ............... G06F 17/243 715/226 |
| 2014/0379371 A1 | 12/2014 | Tran et al. |

(Continued)

OTHER PUBLICATIONS

Drug Enforcement Administration, Pharmacist's Manual, An Informational Outline of the Controlled Substances Act, 2010, United States Department of Justice (Year: 2010).*

(Continued)

*Primary Examiner* — Devin C Hein
(74) *Attorney, Agent, or Firm* — Patent Law Works LLP

(57) ABSTRACT

An electronic image of a paper prescription is received; prescription information is extracted from the image, and a communication is sent to the prescribing physician for approval. If approval is received, delivery of the medication to the patient is approved.

20 Claims, 6 Drawing Sheets

(56) References Cited

U.S. PATENT DOCUMENTS

2015/0242592 A1* 8/2015 Weiss ................. G06F 19/3456
705/2
2015/0324390 A1* 11/2015 Macciola .............. G06F 16/583
707/769

OTHER PUBLICATIONS

Chen, N. etal.. IJDAR (2007) 10: 1. https://doi.org/10.1007/s10032-006-0020-2 (Year: 2007).*
Hiroharu Kawanaka et al. (2012). Document Image Processing for Hospital Information Systems, Modern Information Systems, Dr. Christos Kalloniatis (Ed.), ISBN: 978-953-51-0647-0, InTech (Year: 2012).*
Office Action for EP Application No. 16758325.1, dated Jan. 25, 2019, 7 pgs.

\* cited by examiner

PRESCRIPTION FILLING BY IMAGE

TECHNICAL FIELD

Embodiments of the present invention relate generally to filling pharmaceutical prescriptions and, more particularly, to systems and methods for filling paper prescriptions.

BACKGROUND

While some physicians, dentists, and other medical professionals have begun to issue electronic prescriptions for their patients, many still issue prescriptions written or printed on paper for any of a variety of reasons. For example, the physician may not have the capability to transmit electronic prescriptions, or the patient's preferred pharmacy may not have the capability to receive them. In other instances, the physician or the patient may simply prefer paper prescriptions over electronic ones. Some physicians or pharmacies, in addition, may operate remotely or via mail-order and require paper prescriptions. Furthermore, patients may prefer to refill prescriptions using the prescription information printed on a pill-bottle or other medication label or may need to if their original prescription information is lost or missing.

Filling a paper prescription, however, may be more difficult than filling an electronic prescription; it usually requires that the patient make an in-person visit to a pharmacy to initiate filling and then a second visit to pick up the prescribed medication. Making a trip to initiate filling may be inconvenient or difficult for the patient and may cause the patient to delay filling the prescription or even avoid it entirely, thus delaying or not even initiating taking of his or her prescribed medication. A need therefore exists for a more convenient and simpler way for patients to fill paper prescriptions.

SUMMARY

Embodiments of the present invention include systems and methods for electronic submission of paper prescriptions. In various embodiments, a patient captures an image of a paper prescription with a camera connected to or integrated with a client device and transmits the image to a server. The server extracts prescription information from the image and transmits the information to the prescribing doctor for approval; once the doctor responds with said approval, the server approves shipment of the prescribed medication to the patient.

In one aspect, a system for filling paper prescriptions includes a non-volatile computer memory for storing an electronic image of a paper prescription received from a client device of a patient; a network interface configured for receiving the electronic image and for transmitting and receiving data over a computer network; and a computer processor configured for executing software instructions to: receive, from the client device of the patient via the network interface, the electronic image of the paper prescription; extract prescription information from the electronic image; transmit the prescription information to a prescribing physician for approval; receive a response from the prescribing physician; and approve shipment delivery of prescribed medication to the patient.

In various embodiments, the computer processor is further configured for executing software instructions to communicate with the patient if the prescription information is illegible; the communication may be a telephone call, email, or text message. Delivery of the prescribed medication may include in-person or mail-order delivery. The computer processor may be further configured for executing software instructions to inform the patient if the prescribed medication cannot be approved for mail-order delivery. The prescribed medication may not be able to be shipped because it is a level 2, 3, 4, or 5 drug. The computer processor may be further configured for executing software instructions to re-transmit the prescription information to the prescribing physician if no response is received therefrom and/or to inform the patient if no response is received from the re-transmission. The computer processor may be further configured for executing software instructions to transmit a message to the patient upon receipt of the electronic image, upon beginning of the extraction of information, upon receipt of the response from the prescribing physician, or upon approval of shipment. Transmission of the prescription information to the prescribing physician may include a fax. The response from the physician may include an approval of the transmitted prescription information or a new prescription.

In another aspect, a method for filling paper prescriptions includes receiving, from a client device of the patient via the network interface, an electronic image of the paper prescription; extracting prescription information from the electronic image; transmitting the prescription information to a prescribing physician for approval; receiving a response from the prescribing physician; and approving shipment delivery of prescribed medication to the patient.

In various embodiments, the method further comprises communicating with the patient if the prescription information is illegible. Delivery of the prescribed medication may include in-person or mail-order delivery.

15. The method of claim 14, further comprising informing the patient if the prescribed medication cannot be approved for mail-order delivery. The prescription information may be re-transmitted to the prescribing physician if no response is received therefrom. The patient may be informed if no response is received from the re-transmission. A message may be transmitted to the patient upon receipt of the electronic image, upon beginning of the extraction of information, upon receipt of the response from the prescribing physician, or upon approval of shipment. Transmission of the prescription information to the prescribing physician may include a fax. The response from the physician may include an approval of the transmitted prescription information or a new prescription.

These and other objects, along with advantages and features of the present invention herein disclosed, will become more apparent through reference to the following description, the accompanying drawings, and the claims. Furthermore, it is to be understood that the features of the various embodiments described herein are not mutually exclusive and can exist in various combinations and permutations.

BRIEF DESCRIPTION OF THE DRAWINGS

In the drawings, like reference characters generally refer to the same parts throughout the different views. In the following description, various embodiments of the present invention are described with reference to the following drawings, in which.

DETAILED DESCRIPTION

Figure 1:
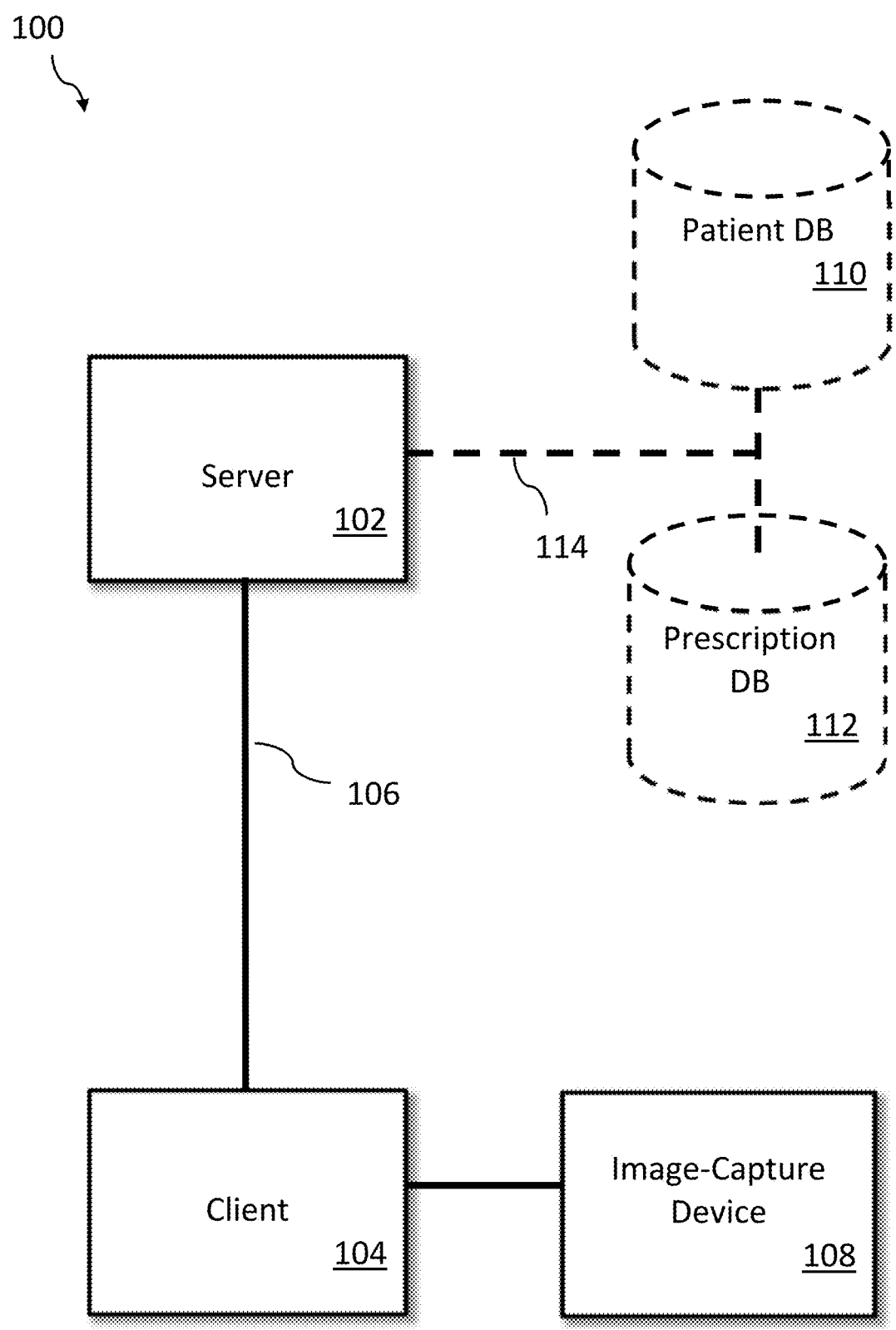
FIG. 1 illustrates a system for electronically processing a paper prescription in accordance with an embodiment of the present invention.

Various embodiments of the present invention include systems and methods for electronically receiving and filling a paper prescription. In various embodiments, with reference to FIG. 1, a computing environment 100 includes a computer server 102 or similar system that is configured to receive, from a remote client device 104, an electronic image of a paper prescription via a network 106 (such as the Internet, telephone network, and/or other network). In various embodiments, the client device 104 is an electronic device such as a smartphone, tablet, or computer and includes or is connected to an image-capture device 108, such as a camera, integrated camera, scanner, or similar device. The server 102 extracts prescription information from the image and transmits the information to the prescribing doctor for approval via the network 106 by telephone, fax, email, or any other means; once the doctor responds with said approval via the network 106 (again, by telephone, fax, email, or any other means), the server 102 approves shipment of the prescribed medication to the patient. In some embodiments, the server 102 accesses a patient database 110 for prescription information and/or a prescription database 112 for patient information via a local or network connection 114. These aspects of the invention are described in greater detail below; one of skill in the art will understand, however, that the invention is not limited to only the configuration of the environment 100 and that other configurations of the server 102 and client device 104 are within the scope of the present invention. For example, any number of servers 102 and clients 104 may be used; in some embodiments, some or all of the functionality of the server 102 may be implemented on the client 104.

Figure 2:
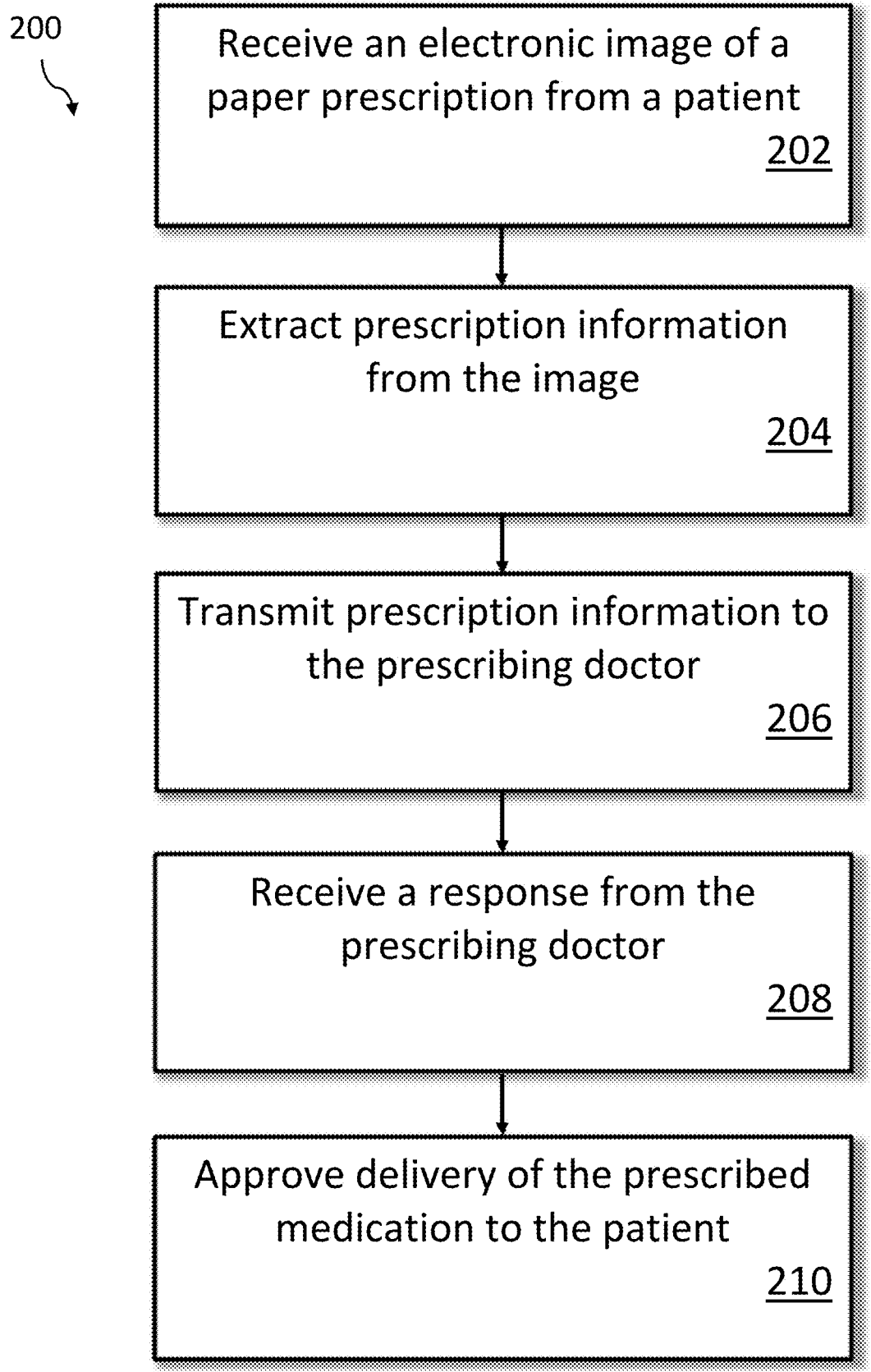
FIG. 2 illustrates a method for electronically processing a paper prescription in accordance with an embodiment of the present invention.

FIG. 2 illustrates a method 200 for electronically filling a paper prescription. In some embodiments, a computer server, such as the server 102 of FIG. 1 or a similar system, receives (202), from a patient, one or more electronic images of a paper prescription over the network 106 from the image-capture device 108 via the client device 104. In other embodiments in which some or all of the functionality of the server 102 is implemented on the client 104, the client 104 receives the electronic image from the image-capture device 108. The images may be in any format, such as JPEG, TIFF, or BMP. The client device 104 may include computer instructions for execution thereon that aid the patient in capturing and transmitting the image, such as a native application, web browser client, or any other similar application or computer instructions; the client application may include a graphical-user interface with, e.g., user-interface elements to display the image before and/or after capture, display the patient's name and/or other information, and/or to capture user input (such as buttons, checkboxes, and text-entry fields). The client application may be dedicated to the capture and transmission of paper prescriptions (and general management thereof) or may be part of a larger patient-care or pharmacy application.

The client application may prompt or otherwise allow the patient to capture one or more images of one or both sides of the prescription paper using, for example, the image-capture device 108. The prescription paper may be a piece of paper, a label affixed to another object (such as a medication bottle, box, syringe, or any other such container), an image displayed on an electronic screen, or any other object capable of bearing prescription information; the present invention is not limited to any particular type of paper or image. In some embodiments, the client device 104 is a smartphone or tablet computer, and the image-capture device 108 is an integrated camera; in other embodiments, the client device 104 is a desktop or laptop computer and is connected (via USB, ETHERNET, or a similar connection) to a camera, webcam, scanner, or similar image-capture device 108. The patient may capture the image of the prescription in accordance with the operation of the particular image-capture device 108. The client application may display the image on the screen of the client device 104 before or after capture so that the patient may ensure that the image is clear and in focus; the client application may guide the patient in taking the image by overlaying, e.g., a boundary box, crosshairs, or other visual aids on the display. Once the client device 104 receives the image from the image-capture device 108, the client application transmits the image (or images) to the server 102 via the network 106. The server 102 may store the data corresponding to the image in volatile or non-volatile storage.

Information is then extracted (204) from the image. In some embodiments, the server 102 extracts the information. In other embodiments, however, the client 104 extracts some or all of the information from the image and transmits the image and/or said extracted information to the server 102; in these embodiments, the server 102 may extract only some information or none of the information (or may re-extract information extracted by the client 104 to verify or compare the results of the extraction by the client 104). The server 102 and/or the client 104 may extract information from the image using any technique known in the art, such as, for example, optical-character recognition, pattern detection, edge detection, one- or two-dimensional bar-code scanning, or any other technique.

Once extracted, the information may be assigned a tag, category, label, or similar identifier based on the nature of the information and/or its context in the image. For example, an extracted string of characters may be compared to a list of medication names (which may be stored in, for example, the prescription database 112); if a match is found, the server 102 and/or client 104 tags the string of characters as a medication name. Similarly, the extracted string of characters may be compared against a list of prescribing doctors associated with the patient (and which may be stored in the patient database 110); if a match is found, the server 102 and/or client 104 tags the string of characters as a doctor name. If the extracted string of characters matches one of a list of pre-defined keywords (such as, for example, "Doctor," "Patient," "Medication," "Dose," etc.), the server 102 and/or client 104 may assume that another extracted string of characters located proximate the keyword in the original image is associated with the keyword and tags/categorizes the other extracted string accordingly. The server 102 and/or client 104 may recognize a particular type or kind of prescription paper appearing in the image by, for example, comparing a format, size, and/or shape of, (font, logo, and/or design appearing in) the image to a database of known formats, sizes, shapes, fonts, logos, and/or designs. Once the type or kind of prescription paper is determined, the server 102 and/or client 104 may then assign tags to extracted text based on known (x,y) positions of corresponding fields in the image. For example, if a given type of prescription paper has a field for medication dosage in its bottom-right corner, the server 102 and/or client 104 assigns text extracted from the bottom-right corner a "dosage" tag. If the server 102 and/or client 104 cannot recognize the type or kind of the prescription paper, a new type or kind may be created with this prescription paper as its first member; future prescription papers may be compared against the new type or kind, thus permitting the server 102 and/or client to learn to recognize new types of prescription papers.

If some of the extracted text cannot be read, parsed, or categorized, the server 102 and/or client 104 may infer the meaning of the unreadable text based on other information extracted from the image, information known about the medication, and/or information known about the patient. If, for example, the medication and/or dosage cannot be determined, the server 102 and/or client 104 may look up the patient's diagnosis and/or medication history in, for example, the patient database 110 to determine one or more likely candidates for the medication and/or dosage. If, for example, the patient is due for renewal of an existing medication or if a diagnosis makes prescription of a particular medication likely, the server 102 and/or client 104 may tag the unreadable text as that medication. In some embodiments, the extracted text includes both readable and unreadable portions; the server 102 and/or client 104 may verify that the determined medication is correct by matching its name to the readable portions of the extracted text. In other embodiments, the server 102 and/or client 104 verifies the determined medication by comparing some or all of the shape of the text in the image with an expected shape.

The server 102 and/or client 104 may test the image for adequacy (i.e., readability) by, for example, performing an optical-character recognition function and testing for recognized characters, by performing an image-processing function such as edge detection and evaluating the results, by measuring a light or contrast level of the image, or by any other method known in the art. If the server 102 determines that the quality of the image is inadequate, the server 102 may transmit a message to the client 104 informing the patient of said inadequacy and optionally requesting that the patient re-capture the image. In another embodiment, the client 104 evaluates the image before, during, or after capture and, if the quality of the image is inadequate, similarly informs the patient. Whether in response to a message from the server 102 or in response to its own determination, the client application may inform the patient of inadequate image quality via text, visual, or audio feedback and direct the patient to improve the quality of the image by, for example, changing the focus of the image-capture device 108, adjusting the distance between the image-capture device 108 and the paper prescription, changing the flash or ambient lighting conditions, and/or re-taking the image.

If some or all of the image is unreadable, the server 102 and/or client 104 may instead or in addition transmit a message to the patient requesting that the patient enter additional information about the image (using, for example, text or voice input) corresponding to a portion of the image that contains unreadable text. For example, if a portion of the image contains text that is too blurry or is written in handwriting too unreadable to be detected using optical character recognition or is located in a section of the image that is too dark for (e.g.) acceptable edge detection, the client application may highlight this section of the image and prompt the patient to enter text or voice input corresponding to the characters or images. For example, if the prescribing doctor's name or signature is unreadable, the client application may prompt the patient to input the name of his or her doctor. In another embodiment, if the medication name or dosage is unreadable, the client application prompts the user for that information. The patient may not know how to spell the name of the medication; in this case, the client application prompts the patient for his or her best guess as to the proper spelling. The client 104 may thereafter transmit the image and/or additional information to the server 102.

The server 102 and/or client 104 may perform one or more steps to detect and flag fraudulent activity on the part of the patient or other submitter. For example, the server 102 and/or client 104 may match the patient name, doctor name, prescription date, medication name, and/or medication dosage against a list of already-filled prescriptions to ensure that the patient is not attempting to re-submit an already-filled prescription; the server 102 and/or client 104 may similarly compare the image against already-submitted images. In other embodiments, the server 102 and/or client 104 compares an image of the prescribing doctor's signature against one or more images of already-captured signatures to ensure that the submitted signature matches and is not forged.

In other embodiments, the electronic image is manually reviewed by a technician who reads the text in the image (including but not limited to the medication name, medication dosage, doctor name, patient name, and/or pharmacy name). The technician may receive input and output directly from the server 102 (via, for example, an attached keyboard, mouse, and monitor) or may connect to the server 102 using another client device 104. The technician may view the image as transmitted by the client 104; in other embodiments, the server 102 and/or client 104 perform some or all of the automated character-recognition steps described above, and the technician reviews and potentially approves the results. For example, the technician may view the image, discern the names of the patient, doctor, medication, dosage, etc., and enter the names into an entry form; in other embodiments, the server 102 and/or client 104 automatically detect the names and wholly or partially populate the entry form for the technician's approval.

The server 102 and/or client 104 may further receive, or otherwise have access to, information identifying the patient. In some embodiments, the client application requires or allows the patient to log into a pre-existing user account hosted on the server 102 (or on a system in communication therewith, such as patient database 110) using, for example, a user name and password associated with the user account. The user account may include information about the patient, such as his or her name, address, phone number, payment information, etc. If the patient executes the client application but does not have a user account preconfigured, the client application may prompt the patient to create one. In other embodiments, the patient is prompted for his or her information (such as name, address, credit-card information, etc.) when executing the client application (prior to or during transmission of the image, for example).

Figure 3:
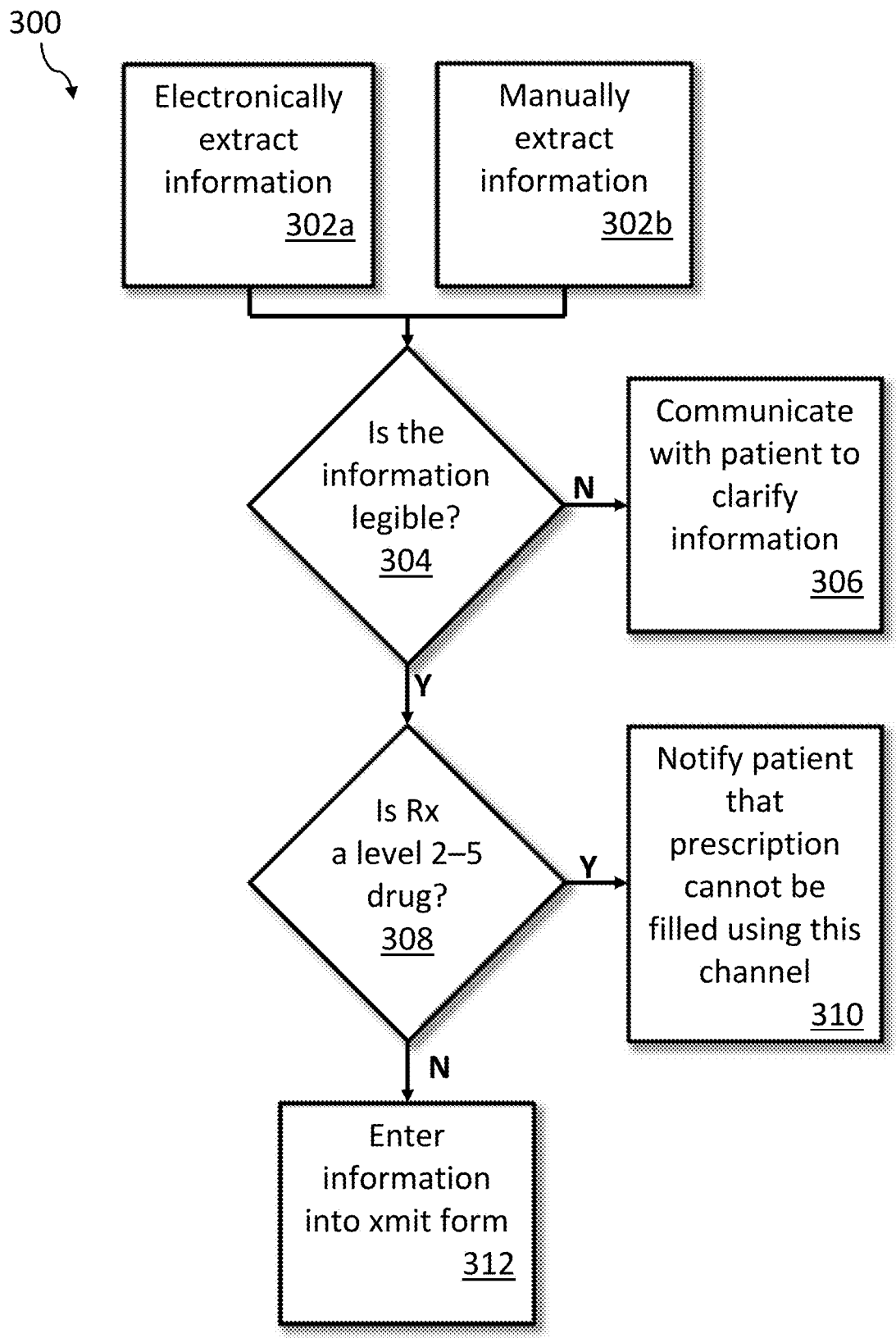
FIG. 3 illustrates a method for extracting information from a paper prescription in accordance with an embodiment of the present invention.

FIG. 3 illustrates a method 300 for extracting information from an image of a prescription that includes illegible handwriting. In alternative first steps, information is extracted from the image either electronically/automatically (302a) or manually (302b). If the information is not legible (304), a communication is sent (306) to the patient for clarification. In one embodiment, this communication includes one or more telephone calls; in other embodiments, the communication includes an email, text message, or in-app message (e.g., a pop-up alert in the client-based software application described above). The patient may respond to the communication using the selected or any other means of communication and include the requested information in the response. The information may then be automatically and/or manually filled (312) in to a transmit form for transmission to the prescribing physician.

In one embodiment, the type of prescription to be filled is checked (308); some types of paper prescriptions may not be able to be filled electronically due to, for example, government regulations. For example, if the medication is a level 2, 3, 4, or 5 drug, the patient may be notified (310) via telephone, email, fax, or any other means that his or her paper prescription cannot be filled electronically. The notification may include instructions for filling the prescription in person and/or a list of one or more pharmacies capable of filling the prescription that are convenient for the patient.

When the information is manually and/or automatically extracted from the image and entered into a transmission form, the form is sent (206) to the prescribing doctor. The form and transmission method may be a fax in order to comply with existing transmission infrastructure; the present invention is not limited, however, to only this form of transmission, and any means of transmission, such as email, text message, or telephone, is within the scope of the present invention. In some embodiments, the prescribing physician operates a physician application on a client 104; the physician application may communicate with the server 104 and display the prescription information to the physician, who may then reject or approve the prescription via user input.

The server 102, client 104, and/or technician may then receive (208) the response from the physician. The response may be an approval or disapproval of the transmitted prescription or a new prescription; the new prescription may contain the same medication, dosage, and other details as the transmitted prescription or may (at the discretion of the physician) contain different details. Any type, format, or content of the response from the physician is within the scope of the present invention. If the response is negative, the patient may be so informed and no further steps may be taken. If the response is positive (i.e., it approves the transmitted prescription or includes a new prescription), the server 102, client 104, and/or technician may approve (210) delivery of the prescribed medication to the patient via, for example, in-person delivery (via a pharmacy, kiosk, or similar medication-dispensing facility), mail-order delivery (via, for example a post office or commercial shipping service), or any other channel of delivery. The owner or operator of the server 102 may be the same entity that stores, selects, and delivers the medication or may contract with another entity that stores, selects, and delivers the medication. If no response is received from the physician within a set time limit (e.g., 48 hours), the form may be re-sent. If still no response is received, a communication (e.g., a telephone call) may be made to the patient to thereby inform the patient of the lack of response.

Figure 4:
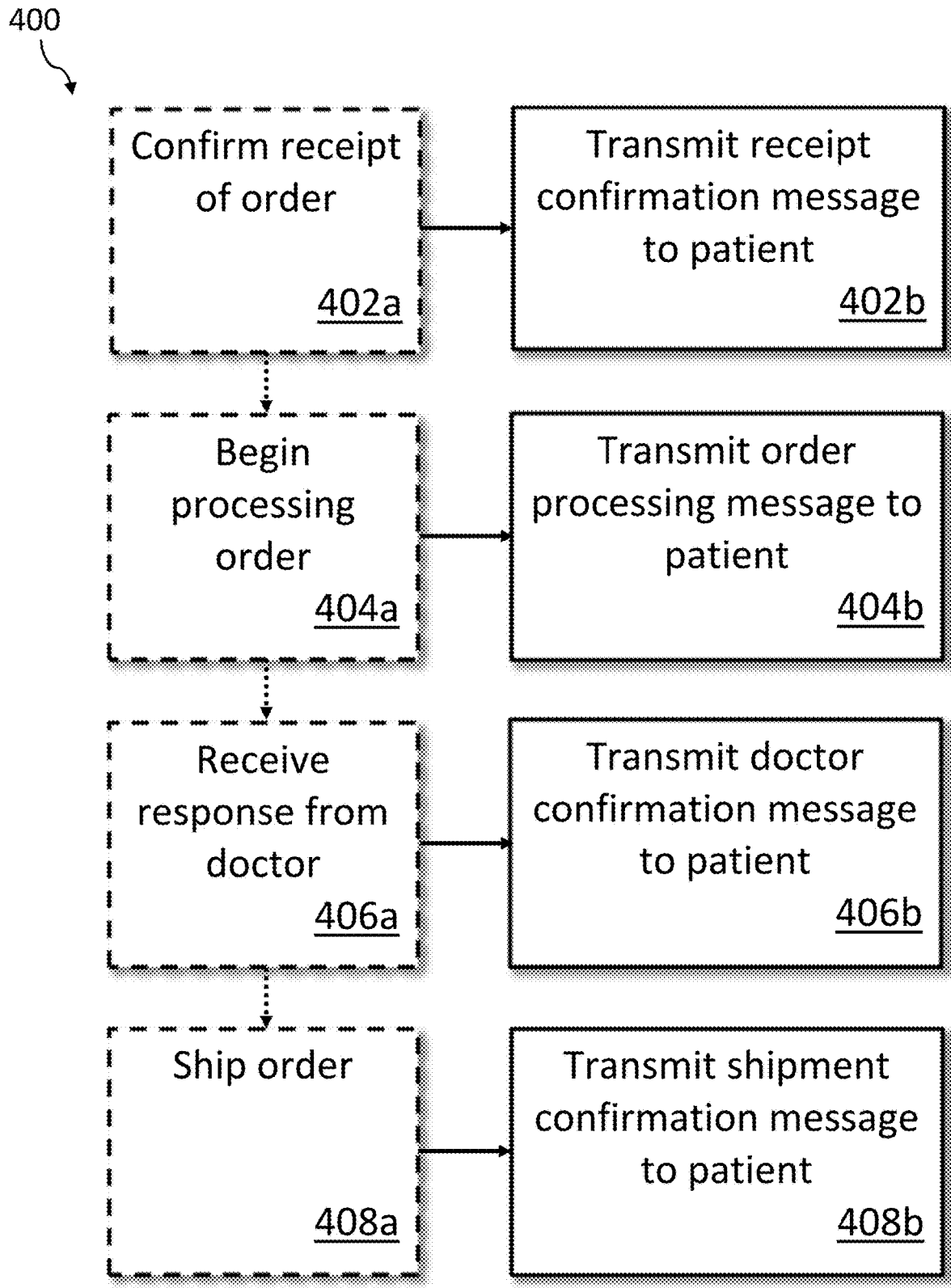
FIG. 4 illustrates a method for sending alerts to a patient in accordance with an embodiment of the present invention.

One or more messages may be transmitted to the patient during one or more of the above-described steps. FIG. 4 illustrates a process flow 400 for generating and sending one or more such messages. In one embodiment, for example, when the server 102 and/or client 104 receives (402a) an order (i.e., receives an image of a paper prescription), a confirmation message is transmitted (402b) to the patient via telephone, fax, email, or any other means. When the server 102, client 104, and/or technician begins processing the order (404a), an order-processing message may be transmitted (404b) to the patient. Similarly, when a response is received from the prescribing physician (406a), a message may be transmitted (406b) to the patient. Finally, in the case of mail-order delivery, when the order is shipped (408a), a shipment order may be transmitted (408b) to the patient.

Figure 5:
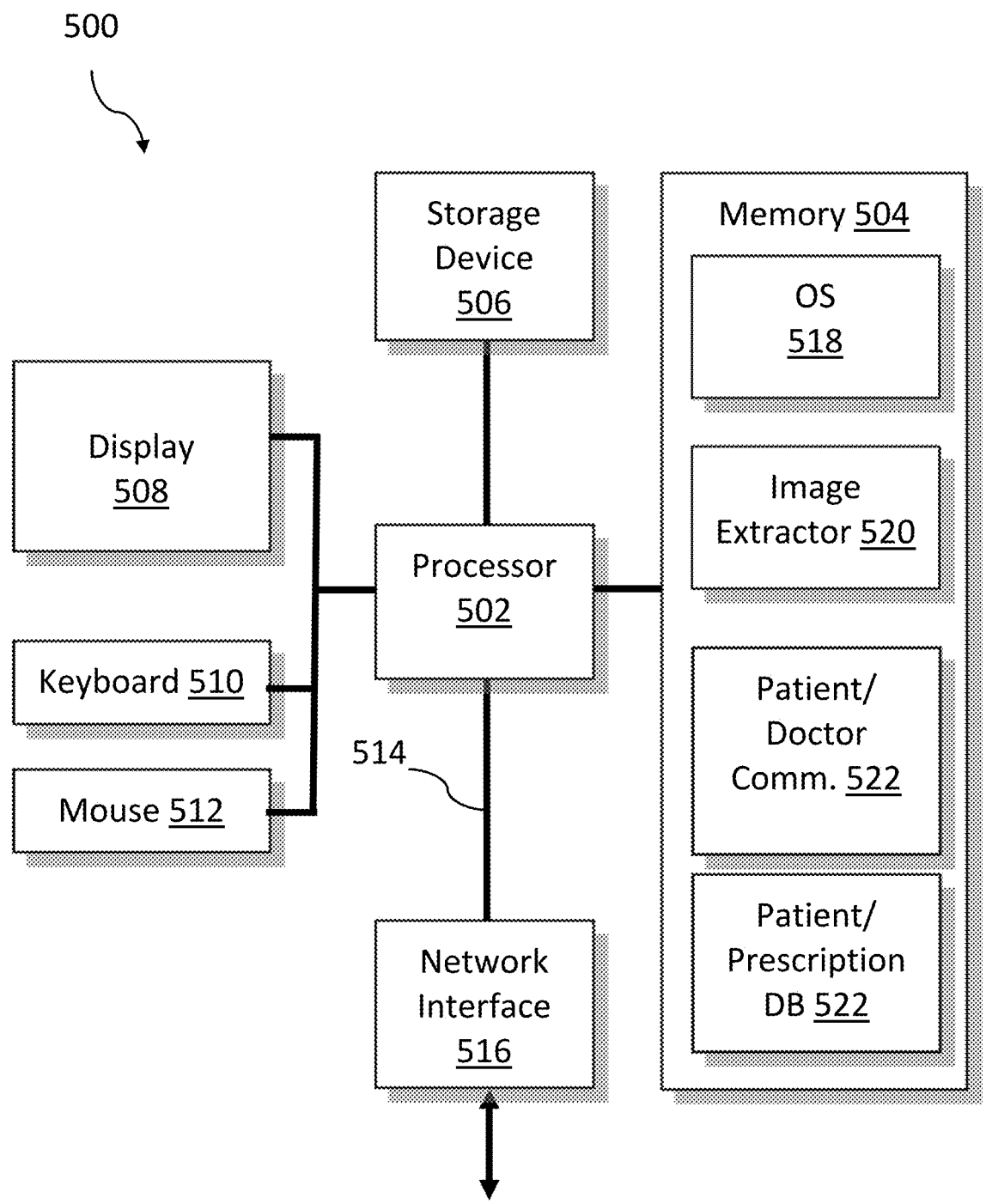
FIG. 5 illustrates a server system for electronically processing a paper prescription in accordance with an embodiment of the present invention.

FIG. 5 is a simplified block diagram of a suitably programmed general-purpose server 500 implementing embodiments of the present invention. The server 500 includes a processor 502 having one or more central processing units (CPUs), volatile and/or non-volatile main memory 504 (e.g., RAM, ROM, or flash memory), one or more mass storage devices 506 (e.g., hard disks, or removable media such as CDs, DVDs, USB flash drives, etc. and associated media drivers), a display device 508 (e.g., a liquid-crystal display (LCD) monitor), user-input devices such as a keyboard 510 and a mouse 512, and one or more buses 514 (e.g., a single system bus shared between all components, or separate memory and peripheral buses) that facilitate communication between these components. A network interface 516 (e.g., a Wi-Fi or ETHERNET port) may be used to connect the computer 500 to the Internet or other network.

The main memory 504 may be used to store instructions to be executed by the processor 502, conceptually illustrated as a group of modules. These modules generally include an operating system 518 (e.g., a Microsoft WINDOWS, Linux, or APPLE OS X operating system) that directs the execution of low-level, basic system functions (such as memory allocation, file management, and the operation of mass storage devices), as well as higher-level software applications, such as a paper-prescription image information extractor 520 and a doctor/patient communicator 522. The various modules may be programmed in any suitable programming language, including, without limitation high-level languages such as C, C++, Java, Perl, Python, or Ruby or low-level assembly languages. The memory 504 may further store input and/or output data associated with execution of the instructions (including, e.g., patient/prescription database 524) as well as additional information used by the various software applications.

Figure 6:
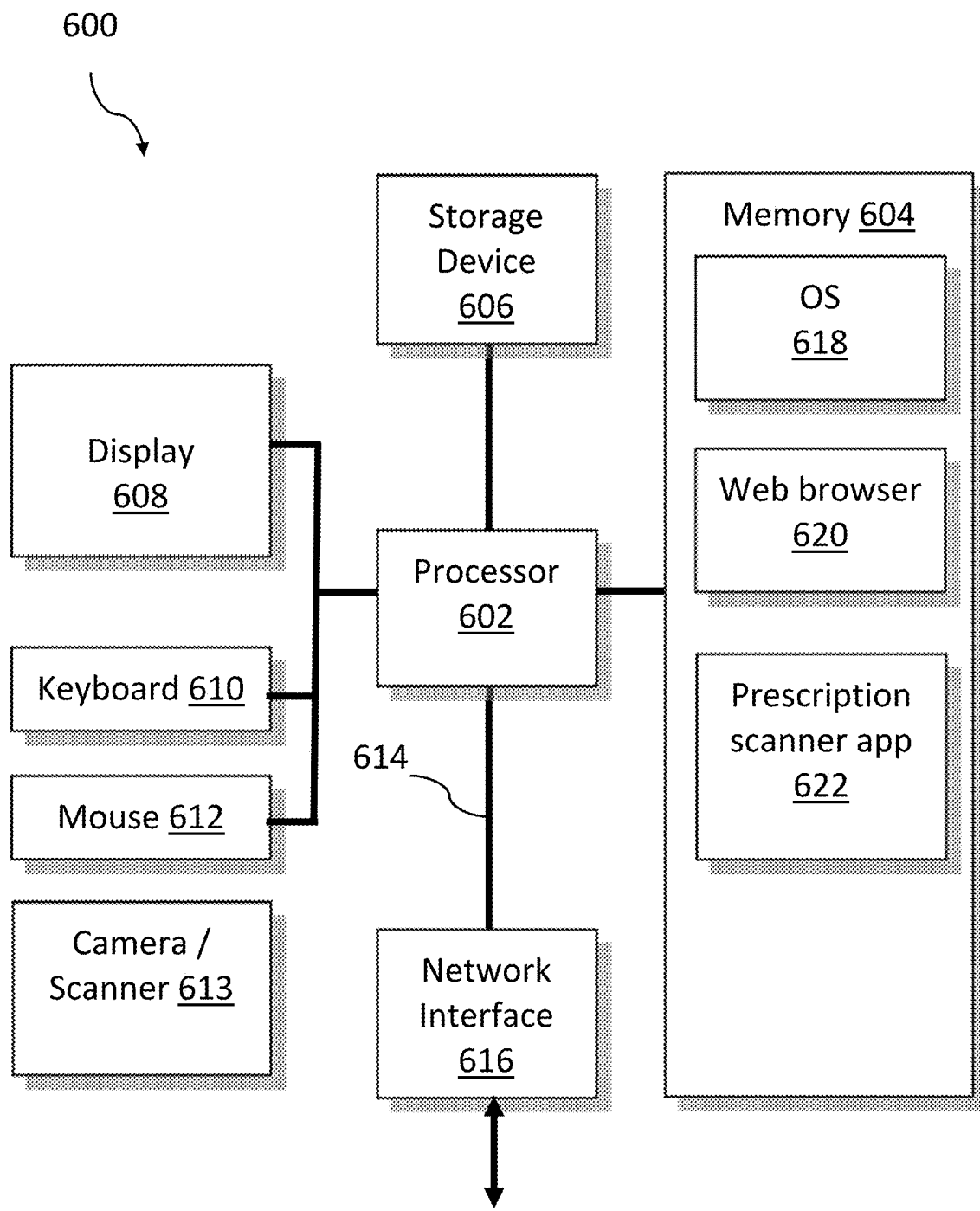
FIG. 6 illustrates a client system for capturing an image of a paper prescription, sending the image to the server, and receiving information regarding the prescription from the server in accordance with an embodiment of the present invention.

FIG. 6 is a simplified block diagram of a suitably programmed client device 600 for capturing information from a user and displaying an order status thereto. Like the server 500, the client device 600 includes a processor 602, a memory 604, a storage device 606, a display 608, a keyboard 610, a mouse 612, buses 614, and a network interface 616. The client 600 may further include a camera/scanner 613 for capturing images. The client 600 and the server 500 may communicate via a network such as the Internet using the network interfaces 516, 616. The user input and output interfaces described herein may be presented to the user via a web browser 620 and/or a client-native application 622.

The server 500 and client 600 are described herein with reference to particular blocks, but this description is not intended to limit the invention to a particular physical arrangement of distinct component parts. The computers 500, 600 are illustrative examples; variations and modifications are possible. Computers 500, 600 may be implemented in a variety of form factors, including server systems, desktop systems, laptop systems, tablets, smartphones or personal digital assistants, and so on. A particular implementation may include other functionality not described herein, e.g., wired and/or wireless network interfaces, media playing and/or recording capability, etc. In some embodiments, one or more cameras may be built into the computer rather than being supplied as separate components. Further, the computer processor may be a general-purpose microprocessor, but depending on implementation can alternatively be, e.g., a microcontroller, peripheral integrated circuit element, a customer-specific integrated circuit ("CSIC"), an application-specific integrated circuit ("ASIC"), a logic circuit, a digital signal processor ("DSP"), a programmable logic device such as a field-programmable gate array ("FPGA"), a programmable logic device ("PLD"), a programmable logic array ("PLA"), smart chip, or other device or arrangement of devices.

It should also be noted that embodiments of the present invention may be provided as one or more computer-readable programs embodied on or in one or more articles of manufacture. The article of manufacture may be any suitable hardware apparatus, such as, for example, a floppy disk, a hard disk, a CD ROM, a CD-RW, a CD-R, a DVD ROM, a DVD-RW, a DVD-R, a flash memory card, a PROM, a RAM, a ROM, or a magnetic tape. In general, the computer-readable programs may be implemented in any programming language. Some examples of languages that may be used include C, C++, or JAVA. The software programs may be further translated into machine language or virtual machine instructions and stored in a program file in that form. The program file may then be stored on or in one or more of the articles of manufacture.

Certain embodiments of the present invention were described above. It is, however, expressly noted that the present invention is not limited to those embodiments, but rather the intention is that additions and modifications to what was expressly described herein are also included within the scope of the invention. Moreover, it is to be understood that the features of the various embodiments described herein were not mutually exclusive and can exist in various combinations and permutations, even if such combinations or permutations were not made express herein, without departing from the spirit and scope of the invention. In fact, variations, modifications, and other implementations of what was described herein will occur to those of ordinary skill in the art without departing from the spirit and the scope of the invention. As such, the invention is not to be defined only by the preceding illustrative description.

What is claimed is:

1. A system for filling paper prescriptions, the system comprising:
   a non-volatile computer memory for storing an electronic image of a paper prescription received from a client device of a patient;
   a network interface configured for receiving the electronic image and for transmitting and receiving data over a computer network; and
   a computer processor configured for executing software instructions to:
   receive, from the client device of the patient via the network interface, the electronic image of the paper prescription;
   receive, from the client device of the patient via the network interface, prescription information extracted from the electronic image;
   re-extract the prescription information extracted by the client device of the patient from the electronic image by identifying features of the electronic image, determining a type of prescription in the electronic image using the identified features, and determining the prescription information from the type of prescription based on positions of fields corresponding to the prescription information;
   verify the prescription information based on comparing the extracted information and the re-extracted information;
   determine whether a portion of the electronic image is unreadable;
   responsive to determining that the portion of the electronic image is unreadable, infer information from the unreadable portion based on other information extracted from the electronic image and information about the patient;
   transmit the prescription information to a prescribing physician for approval;
   receive a response from the prescribing physician; and
   approve delivery of a prescribed medication to the patient.

2. The system of claim 1, wherein the computer processor is further configured for executing software instructions to communicate with the patient if the portion of the electronic image is unreadable.

3. The system of claim 2, wherein the communication is a telephone call, email, or text message.

4. The system of claim 1, wherein the delivery of the prescribed medication comprises in-person or mail-order delivery.

5. The system of claim 4, wherein the computer processor is further configured for executing software instructions to inform the patient if the prescribed medication cannot be approved for mail-order delivery.

6. The system of claim 5, wherein the prescribed medication cannot be shipped because it is a level 2, 3, 4, or 5 drug.

7. The system of claim 1, wherein the computer processor is further configured for executing software instructions to re-transmit the prescription information to the prescribing physician if no response is received therefrom.

8. The system of claim 7, wherein the computer processor is further configured for executing software instructions to inform the patient if no response is received from the re-transmission.

9. The system of claim 1, wherein the computer processor is further configured for executing software instructions to transmit a message to the patient upon receipt of the electronic image, upon beginning of the extraction of prescription information, upon receipt of the response from the prescribing physician, or upon approval of shipment.

10. The system of claim 1, wherein transmission of the prescription information to the prescribing physician comprises a fax.

11. The system of claim 1, wherein the response from the prescribing physician comprises an approval of the transmitted prescription information or a new prescription.

12. A method for filling paper prescriptions comprising:
   receiving, from a client device of a patient via a network interface, an electronic image of a paper prescription;
   receiving, from the client device of the patient via the network interface, prescription information extracted from the electronic image;
   re-extracting the prescription information extracted by the client device of the patient from the electronic image by identifying features of the electronic image, determining a type of prescription in the electronic image using the identified features, and determining the prescription information from the type of prescription based on positions of fields corresponding to the prescription information;

verifying the prescription information based on comparing the extracted information and the re-extracted information;

determining whether a portion of the electronic image is unreadable;

responsive to determining that the portion of the electronic image is unreadable, inferring information from the unreadable portion based on other information extracted from the electronic image and information about the patient;

transmitting the prescription information to a prescribing physician for approval;

receiving a response from the prescribing physician; and approving delivery of a prescribed medication to the patient.

13. The method of claim 12, further comprising communicating with the patient if the portion of the electronic image is unreadable.

14. The method of claim 12, wherein the delivery of the prescribed medication comprises in person or mail-order delivery.

15. The method of claim 14, further comprising informing the patient if the prescribed medication cannot be approved for mail-order delivery.

16. The method of claim 12, further comprising re-transmitting the prescription information to the prescribing physician if no response is received therefrom.

17. The method of claim 16, further comprising informing the patient if no response is received from the re-transmission.

18. The method of claim 12, further comprising transmitting a message to the patient upon receipt of the electronic image, upon beginning of the extraction of prescription information, upon receipt of the response from the prescribing physician, or upon approval of shipment.

19. The method of claim 12, wherein transmission of the prescription information to the prescribing physician comprises a fax.

20. The method of claim 12, wherein the response from the prescribing physician comprises an approval of the transmitted prescription information or a new prescription.

* * * * *